(12) United States Patent
Leichner

(10) Patent No.: US 10,115,482 B2
(45) Date of Patent: Oct. 30, 2018

(54) REFLEXIVE EDUCATION: A METHOD FOR AUTOMATED DELIVERY OF EDUCATIONAL MATERIAL LINKED TO OBJECTIVE OR SUBJECTIVE DATA

(75) Inventor: Robert C. Leichner, Menlo Park, CA (US)

(73) Assignee: Koninklijke Philips N.V., Eindhoven (NL)

( * ) Notice: Subject to any disclaimer, the term of this patent is extended or adjusted under 35 U.S.C. 154(b) by 3191 days.

(21) Appl. No.: 12/091,100

(22) PCT Filed: Oct. 2, 2006

(86) PCT No.: PCT/IB2006/053592
§ 371 (c)(1),
(2), (4) Date: Apr. 22, 2008

(87) PCT Pub. No.: WO2007/049163
PCT Pub. Date: May 3, 2007

(65) Prior Publication Data
US 2008/0268413 A1 Oct. 30, 2008

Related U.S. Application Data

(60) Provisional application No. 60/729,571, filed on Oct. 24, 2005.

(51) Int. Cl.
*G16H 10/60* (2018.01)
*G16H 40/63* (2018.01)
(52) U.S. Cl.
CPC ............. *G16H 10/60* (2018.01); *G16H 40/63* (2018.01)
(58) Field of Classification Search
CPC .................. G16H 10/60; G16H 40/63

USPC ..... 705/2, 3; 434/307 R, 365; 709/217, 224; 600/481, 567, 300
See application file for complete search history.

(56) References Cited

U.S. PATENT DOCUMENTS

| 5,601,435 A | * | 2/1997 | Quy .......................... 434/307 R |
| 5,879,163 A | | 3/1999 | Brown et al. |
| 5,887,133 A | | 3/1999 | Brown et al. |

(Continued)

FOREIGN PATENT DOCUMENTS

| JP | 9062651 A | 3/1997 |
| JP | 2002259570 A | 9/2002 |

(Continued)

OTHER PUBLICATIONS

Lorig et al, "Self-Management Education: History, Definition, Outcomes and Mechanisms", The Society of Behavioral Medicine, 2003, pp. 1-7.

(Continued)

*Primary Examiner* — John A Pauls

(57) ABSTRACT

A health management system (10) comprises educational content sessions (150, 152, . . . ) each being directed toward achieving a health management goal. A user interface (48) is configured for presenting the content sessions (150, 152, . . . ). At least one feedback path (48, 82, 120, 122) provides at least one input which includes an item of interest. A content flow engine (170) configured to automatically select the content sessions (150, 152) based on the at least item of interest and on content flow rules and initiate presentation of the selected content sessions via the user interface (48).

17 Claims, 4 Drawing Sheets

(56) References Cited

U.S. PATENT DOCUMENTS

Figure 1:
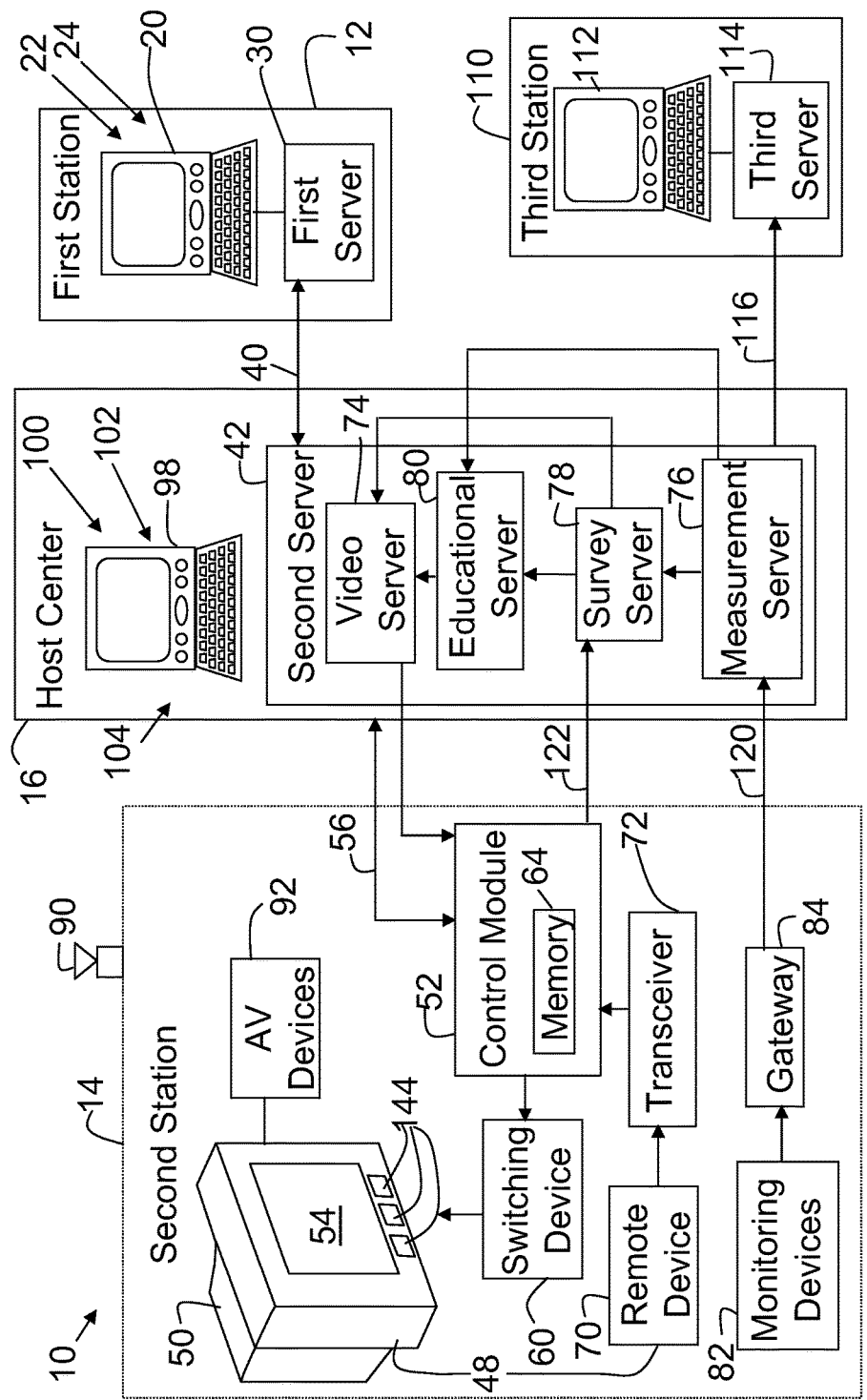

| | | | |
|---|---|---|---|
| 5,897,493 | A | 4/1999 | Brown |
| 5,960,403 | A | 9/1999 | Brown |
| 5,997,476 | A | 12/1999 | Brown |
| 6,101,478 | A | 8/2000 | Brown |
| 6,168,563 | B1 | 1/2001 | Brown |
| 6,171,112 | B1 | 1/2001 | Clark et al. |
| 6,248,065 | B1 | 6/2001 | Brown |
| 6,249,809 | B1* | 6/2001 | Bro ............... 709/217 |
| 6,290,646 | B1 | 9/2001 | Cosentino et al. |
| 6,375,469 | B1 | 4/2002 | Brown |
| 6,454,705 | B1 | 9/2002 | Cosentino et al. |
| 6,723,045 | B2 | 4/2004 | Cosentino et al. |
| 6,755,783 | B2 | 6/2004 | Cosentino et al. |
| 6,968,375 | B1 | 11/2005 | Brown |
| 2001/0031913 | A1 | 10/2001 | Ito et al. |
| 2002/0133377 | A1 | 9/2002 | Brown |
| 2002/0188477 | A1* | 12/2002 | Ackermann et al. ......... 705/3 |
| 2003/0036683 | A1* | 2/2003 | Kehr et al. ............ 600/300 |
| 2003/0069753 | A1 | 4/2003 | Brown |
| 2003/0130595 | A1* | 7/2003 | Mault ................. 600/567 |
| 2003/0163351 | A1 | 8/2003 | Brown et al. |
| 2003/0187336 | A1 | 10/2003 | Odagiri et al. |
| 2004/0019259 | A1 | 1/2004 | Brown et al. |
| 2004/0102685 | A1 | 5/2004 | Cosentino et al. |
| 2004/0117207 | A1 | 6/2004 | Brown |
| 2004/0117208 | A1 | 6/2004 | Brown |
| 2004/0117209 | A1 | 6/2004 | Brown |
| 2004/0219500 | A1 | 11/2004 | Brown et al. |
| 2004/0243443 | A1 | 12/2004 | Asano et al. |
| 2005/0026131 | A1* | 2/2005 | Elzinga et al. ......... 434/365 |
| 2005/0027562 | A1 | 2/2005 | Brown |
| 2005/0080652 | A1 | 4/2005 | Brown |
| 2005/0086083 | A1 | 4/2005 | Brown |
| 2005/0172021 | A1 | 8/2005 | Brown |
| 2005/0172022 | A1 | 8/2005 | Brown |
| 2005/0228883 | A1 | 10/2005 | Brown |
| 2005/0235060 | A1* | 10/2005 | Brown ................ 709/224 |
| 2005/0273509 | A1 | 12/2005 | Brown |
| 2006/0004611 | A1 | 1/2006 | Brown |
| 2006/0015017 | A1 | 1/2006 | Cosentino et al. |
| 2006/0064020 | A1* | 3/2006 | Burnes et al. ......... 600/481 |
| 2006/0080152 | A1 | 4/2006 | Brown |
| 2006/0089969 | A1 | 4/2006 | Brown et al. |
| 2006/0100910 | A1 | 5/2006 | Brown |
| 2008/0268413 | A1 | 10/2008 | Leichner |

FOREIGN PATENT DOCUMENTS

| | | |
|---|---|---|
| JP | 2002259572 A | 9/2002 |
| JP | 2002297797 A | 10/2002 |
| JP | 2003030335 A | 1/2003 |
| JP | 2003296464 | 10/2003 |
| JP | 2004133669 | 4/2004 |
| JP | 2004135762 A | 5/2004 |
| JP | 2005284910 A | 10/2005 |
| WO | 98/50873 A1 | 11/1998 |
| WO | 01/77665 A2 | 10/2001 |
| WO | 02/25551 A1 | 3/2002 |
| WO | 02/067775 A1 | 9/2002 |
| WO | 04/053652 A2 | 6/2004 |
| WO | 05/022439 A2 | 3/2005 |

OTHER PUBLICATIONS

Keller, "Choices and Changes" A New Model for Influencing Patient Health Behavior, JCOM, vol. 4, No. 6, Nov./Dec. 1997, pp. 33-36.

Huang, Set-top box market: Concept and objectives, DSP Engineering, Summer 2001, 5 pages.

Ouwens et al, "Integrated care programmes for chronically ill patients: a review of systematic reviews", International Journal for Quality in Health Care, vol. 17, No. Jan. 21, 2005, pp. 141-146.

Panova et al, "Study of the growth atmosphere effect on optical and scintillation characteristics of large CsI(TI) crystals", Journal of Crystal Growth 198/199, 1999, pp. 865-868.

"DMPC Cites Five Best DM Ideas of 2004", Disease management News, vol. 10, No. 2, Jan. 25, 2005, 2 pages.

"Citizen Centered Health & lifestyle Management via Interactive TV: The PANACEIA Health System", Information Society Technologies, Panaceia-iTV, www.itv4health.org, 2001, 21 pages.

"Citizen Centered Health and Lifestyle Management via Interactive TV: The Panaceia Health System", Cyberce Integrated Electronic Commerce Solutions, Panaceia iTV, http://www.cyberce.gr/gr/rd/panaceia.shtml, Jul. 29, 2005.

Philips Press Information, "Philips to begin pilot study of TV-based solution to help patients manage their health from home", Oct. 15, 2004, 3 pages.

Philips Press Information, "U.S. study shows chronic disease patients embrace Philips personalized TV-based interactive healthcare platform to manage disease from home" Jun. 8, 2005, 2 pages.

Philips Press Information, "Philips and Achmea to Launch First European Pilot Study of TV-Based System for Patients to Manage Health at Home", Jun. 8, 2005, 3 pages.

* cited by examiner

REFLEXIVE EDUCATION: A METHOD FOR AUTOMATED DELIVERY OF EDUCATIONAL MATERIAL LINKED TO OBJECTIVE OR SUBJECTIVE DATA

The following relates to the health management arts. It finds particular application in conjunction with the remote interactive outpatient health monitoring and training at the patient's home and will be described with the particular reference thereto. It also finds application in conjunction with patients monitoring and training at the retirement communities, assisted living homes, and the like.

The outpatient or remote health care management system typically connects chronically ill patients and health care providers via interactive health care communication platform, which, for example, uses the patient home television set, or computer terminal. The patients use the medical devices which are installed in their homes to measure vital signs such as blood pressure, heart rate and weight. The patient's biometric data is automatically sent via secured cable or satellite connection links to the supervising health care providers. The health care providers monitor the patients health by setting up the flags for clinical reviews if one of the vital sign measurements falls outside the normal range. In addition, the health care professionals can support the patients by sending them reminders, educational videos, and the like. The patients access such materials through the home television set.

Current methods of providing information to patients are often inefficient and ineffective. Moreover, current methods often only provide information generically to patients according to a medical condition and do not account for specific conditions and needs of the individual patient.

One way to provide individual care information to patients requires access to health care professionals via the telephone or other medium. For example, if the patients require information they may contact their physician's office and speak to a nurse or other health care professional. Alternatively, each nurse of a physician's office may be assigned to certain patients and will contact the patients periodically to render information and care based on each patient's current condition and needs. This method is costly and puts a heavy load on medical personnel. In addition, patients often will not actively solicit information for preventive care; and rather will seek assistance when the care required is urgent.

Another approach is to establish a system which includes a feedback provided by measurements of patients physiological parameters and communicating the measurement results to a physician for analysis. The physician then selects educational material based on analysis of the provided physiological parameter measurement values and sends the patient educational material. However, staffing shortages and labor costs make such method burdensome.

There is a need for a method and apparatus adapted to provide health care information to patients that overcomes at least some of the shortcomings described above.

In accordance with one aspect, a health management system is disclosed. Educational content sessions are being directed toward achieving a health management goal. A user interface is configured for presenting the content sessions. At least one feedback path provides at least one input which includes an item of interest. A content flow engine is configured to automatically select the content sessions based on the at least item of interest and on content flow rules and initiate presentation of the selected content sessions via the user interface.

In accordance with another aspect, a health management system is disclosed. An educational server communicates with a plurality of patients. The educational server stores at least: a plurality of content sessions directed toward achieving a health management goal, and a plurality of patient profiles each corresponding to a respective patient. AO content flow engine is configured to control presentation of content sessions to each patient based on at least one feedback input from the patient and on content flow rules.

In accordance with another aspect, a health management method is disclosed. At least one physiological condition input of interest is received. Presentation of educational content sessions is automatically started based on the physiological condition input and on content flow rules.

In accordance with another aspect, a user interface, accessible by a user, for receiving and sending information to and from a remote station via at least one server, is disclosed. A display is configured for presenting an educational content session transmitted by the server, the educational content session is generated by the server in response to receiving an item of interest from the user interface and is directed toward achieving a health management goal.

The following may take form in various components and arrangements of components, and in various process operations and arrangements of process operations. The drawings are only for the purpose of illustrating preferred embodiments and are not to be construed as limiting the following.

Figure 2:
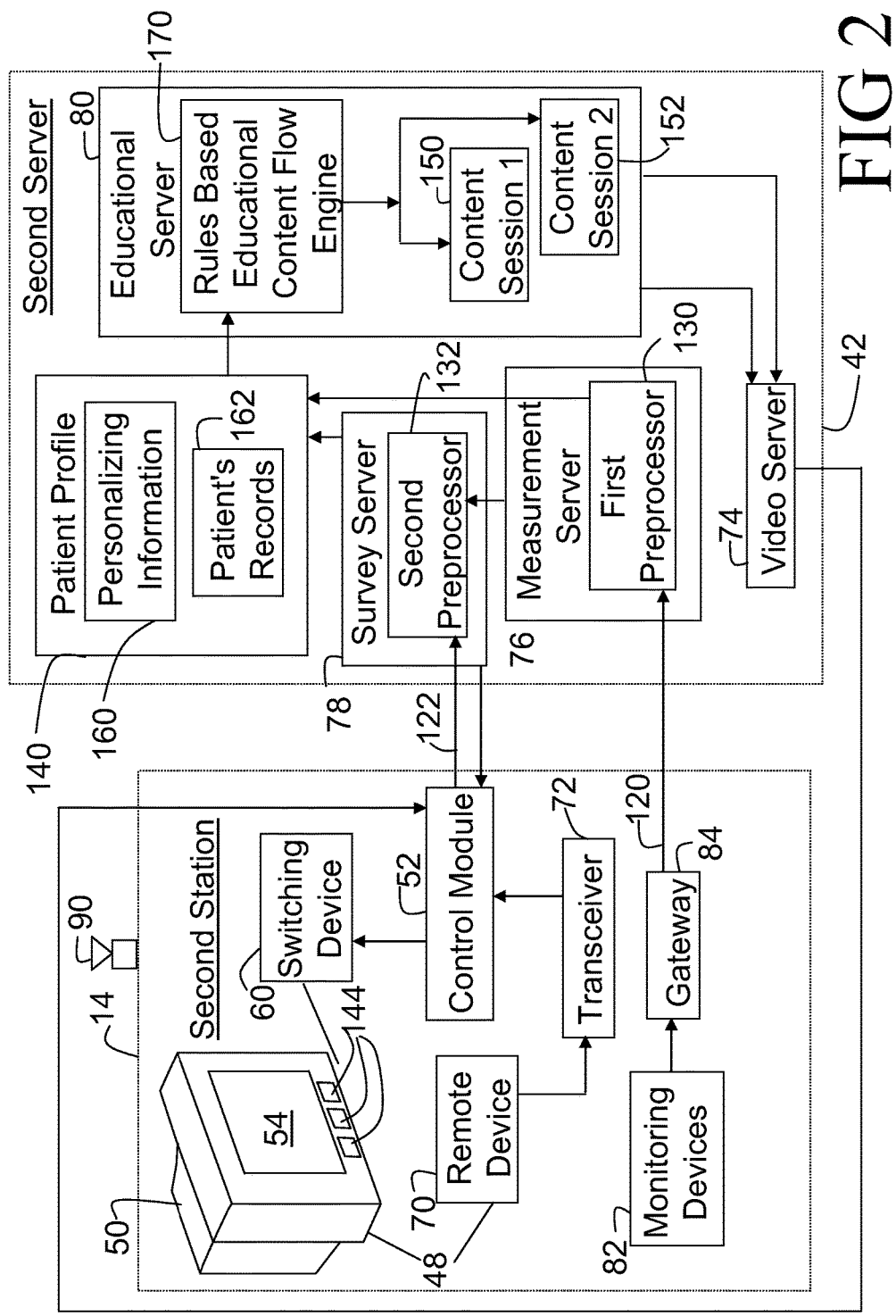
Figure 3:
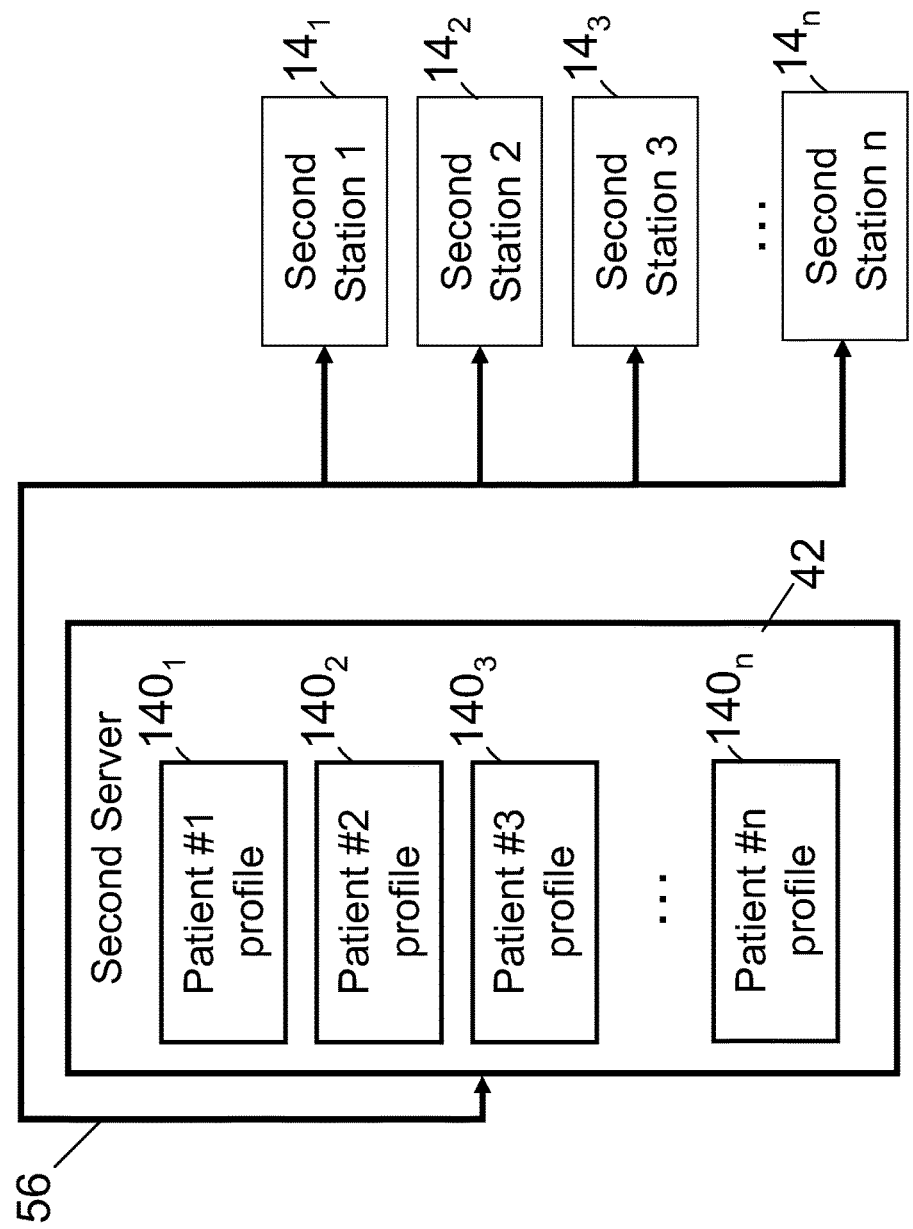
Figure 4:
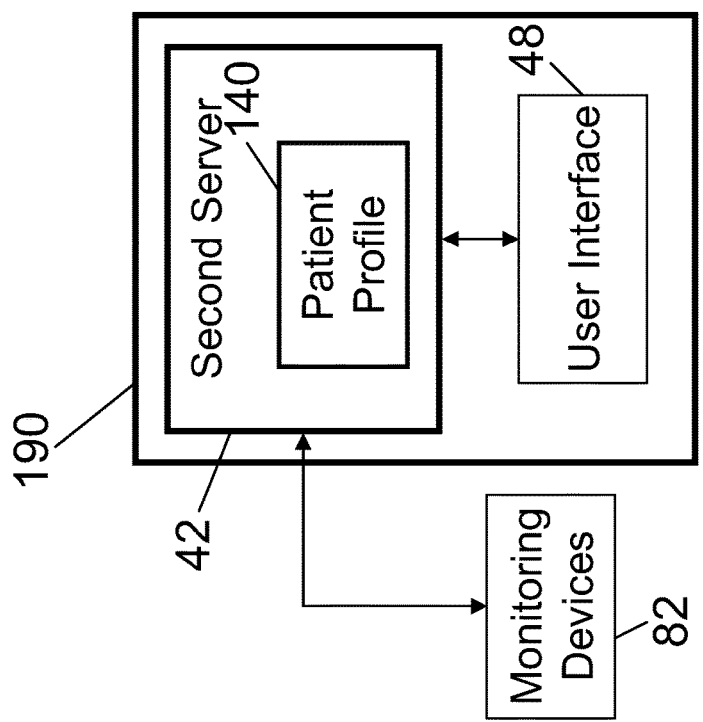

FIG. 1 diagrammatically shows principal components of an example health management system;

FIG. 2 diagrammatically shows a detailed portion of the health management system;

FIG. 3 diagrammatically shows a suitable relatively centralized arrangement of components of the health management system of FIG. 1; and FIG. 4 diagrammatically shows a suitable relatively decentralized arrangement of components of the health management system of FIG. 1.

With reference to FIG. 1, a health management system 10 includes first and second stations 12, 14 and a host center 16. The first or care provider station 12 is located, for example, at a care provider site such as a physician's office or hospital and includes a terminal 20. One example of the terminal 20 is a personal computer which includes an appropriate software 22, such as user interface software, and hardware 24, for interfacing with the host center 16 and the second station 14. The terminal 20 is connected to a first server 30 via an intranet connection as known in the art.

Of course, it is contemplated that the health management system 10 can include a plurality of the first stations 12, a plurality of host centers 16 and a plurality of second stations 14 as appropriate for an application.

A first link 40 provides the connection between the first station 12 and the host center 16. Alternatively, the first station 12 is a wireless station of a wireless local area network (LAN) or wireless wide are network (WAN).

The second or patient station 14 includes a user or patient interface 48 including a television set 50 or other patient display device which is located in a patient's home or dwelling. The user interface 48 further includes a control module or processor or algorithm or means 52, such as set-top box, which interfaces with a video display 54 of the television set 50. The control module 52 converts and displays data from analog cable, digital cable, satellite, or digital broadcast television to a standard channel frequency, e.g. channel number, for display, for example, on a standard analog television set 50. In one embodiment, the control module 52 further receives on or off-air digital or conventional analog television (DTV) signals from a cable or satellite provider or local broadcast TV for display on a DTV monitor. The control module 52 also receives signals such as digital or analog television format signals and patient information signals from the host center 16 via a second link 56. The examples of the second link 56 are wired connection, wireless connection, satellite connection, fiber optic connection, and the like.

The control module 52 is connected to the video display 54 via a switching device or algorithm or means 60 such as an audio/video (AV) switching device as known in the art. The switching device 60 provides switching between television reception from the tuner of the display 54 (or VCR, DVD or the like) and patient information reception/transmission from/to the host center 16. Alternatively, any other known type of input device adapted to provide an interface to the video display 54 is used.

For example, the patient information signals include information, instructions and queries that are displayed on the video display for information, action, and the like. The patient information signals includes video and audio health issue programs, audio programs, video messages and audio messages, reminders to send health or biometric information, and the like. For example, the control module 52 can include a memory 64 so that patient information signals are stored for later use, e.g. time-shifted display. When the switching device 60 is configured to transmit the patient information signals, the control module 52 retrieves the patient information signals from the memory 64 to the display 54 or forwards the signals as received. The user interface further includes a remote interface device 70 which provides signals to an infrared transceiver 72. Signals from the transceiver 72 are provided to the control module 52 and function to select video input to the video display 54, input patient information, and the like. In one embodiment, the remote interface device 70 is a remote control device such as one commonly used in the home entertainment systems. In another embodiment, the remote interface device 70 is a computer input interface device, such as a keyboard or a mouse.

The host center 16 is centralized and includes various servers for specific functions. The examples of servers of the host center 16 are a video server 74 which provides pertinent video content to the display 54, a measurement server 76, a survey server 78 which generates surveys, an educational server 80 which automatically generates and delivers medically oriented educational sessions, as described in detail below, and others. However, it is also contemplated that the host center 16 is distributed, with different components or sub-centers hosting different functions. Alternatively, there may be a plurality of host centers 16 that connect a plurality of second stations 14 with one or more first stations 12.

In one embodiment, the second station 14 includes a set of patient monitoring or biometric devices 82. The examples of the patient monitoring devices 82 include a weight scale, a blood pressure device, an electrocardiogram, an electroencephalogram, an oximeter, a brain wave measuring device, a respiration monitor, a thermometer, and the like. In a typical arrangement, the user is located at a dwelling such as a house, apartment, assisted living apartment, or so forth, and does not have ready access to medical personnel. Accordingly, in some embodiments the biometric devices 82 are advantageously designed to be simple to operate. For example, a fingertip $SpO_2$ monitor can be used to provide both saturated blood oxygen level and heart rate simply by clipping the fingertip monitor onto the patient's fingertip. The biometric devices can be wireless devices which are worn by the patient and communicate biometric reading continuously or at intervals to the host center, can be cabled devices which the patient uses one or more times a day to take readings, or the like. Additionally, or alternatively, certain measurements may be manually entered by the patient via the remote device 70. Alternatively, the biometric device 82 can be implanted in the patient, such as a sensor on a pacemaker, on an infusion pump, and the like. Collected monitored or manual patient data are provided to a measurement gateway 84, which transmits the data to the measurement server 76 for processing and use.

Other exemplary user interface devices are a personal computer (PC), personal digital assistant (PDA), a mobile phone, a portable computer, automated voice response system and the like. As such, the display is accordingly a computer monitor, handheld communication device display, such as a portable phone, cellular phone or PDA.

In one embodiment, the second station 14 includes an RF interface 90 such as an antenna and audio/video (AV) devices 92 which provide links to the second station 14. The examples of the AV devices 92 are a video cassette recorder (VCR), a digital video disc (DVD) player, a cable box, and the like.

The host center 16 includes a host center terminal 98 including appropriate hardware 100, software 102 and communications links 104 to enable connectivity between the first and second stations 12, 14.

Optionally, the health management system 10 includes an information or third station 110 which provides access to the patient information to the authorized users, such as selected family members and friends, via an access terminal 112 connected to a third server 114. The examples of the access terminal 112 are a personal computer, a video display including a control module, a PDA, a portable computer, a cellular telephone, and the like. The connection of the third station 110 to the host center 16 may be a third link 116 wired or wireless connection.

With continuing reference to FIG. 1, the survey server 78 generates unique surveys which are the content controlled or regulated by feedback from a patient or user. The term "patient" as used herein encompasses users or patients recovering from surgery, stroke, heart failure, or another condition, patients suffering a chronic illness that is being treated on an out-patient basis, or so forth. The term "patient" also encompasses other users of the health management system 10 who may be generally healthy but who are following a health management program assisted by the system 10 to maintain fitness, control weight, avoid osteoporosis, or otherwise maintain a healthy condition or make health-related lifestyle modifications.

In the example system 10 of FIG. 1, the feedback paths include the user interface 48 that enables the user to provide responsive input to the survey server 78. Feedback provided by the user interface 48 may include answers to questions posed by the content, or answers to surveys, quizzes, tests, questionnaires, or the like. The feedback paths also include one or more biometric devices 82 that monitor biometric parameters of the patient.

With reference to FIG. 2, at least one of the measurement server 76 and survey server 78 receives a respective responsive input via respective one of first and second feedback path 120, 122. Optionally, first and second pre-processors 130, 132 of the respective measurement and survey servers 76, 78 may perform pre-processing of the input before using it for controlling content flow. The examples of pre-processing are filtering of measurement data for erroneous measurements and survey data for erroneous entries.

In one embodiment, the patient interface 48 receives reflexive surveys. As used herein, the term "reflexive" survey means any survey that is generated in response (e.g., reflexively) to some subjective or objective trigger. For reference, the other survey types include (a) "scheduled", for those that are calendar-driven, and (b) "one-time", for a survey that is specified explicitly by a physician or care provider. The survey server 78 generates surveys based on objective or subjective data, such as how one feels, abnormal vital signs, clinically significant data, or a prior completed (or not completed in time) survey. The user interface 48 enables the patient to input answers to the survey. The survey answers represent a portion of the second feedback path 122 via which the survey answers are forwarded to the survey server 78.

More specifically, the survey server 78 generates the reflexive survey based on one or more triggering events in the monitored vital signs measurement data which is included in the first feedback path 120 and forwarded to the measurement server 76. The first pre-processor 130 optionally filters the vital signs measurement values to eliminate erroneous measurements. The filtered measurement values are forwarded to the survey server 78. For example, for a patient having an abnormal heart rate, the survey server 78 generates a reflexive survey designed to query the patient about his heart or other conditions such as a change in a lifestyle that might have affected the heart. The survey server 78 customizes the reflexive survey on a dynamic basis and/or uses previously developed questions and answers accordingly to the triggering event which generates the item of interest. For example, a received abnormal response to the survey is compared to a predetermined reflexive survey. The item of interest varies between applications and patients, however, the item of interest covers any aspect of the patient that is deemed interesting, including any abnormal or medically significant data, patient diagnosis information, patient mental or physical state.

As another example, the survey server 78 generates unique surveys for the patient based on at least one of the first and second reported feedback, on a patient profile 140 and pre-configured thresholds. The preconfigured thresholds used by the survey server 78 can be of absolute value or a percentage of change from a previous value. The threshold could apply to a 'score' of some other subjective data (such as answers to a previous survey).

In one embodiment, the reflexive survey includes a list of questions, possible answers from which the patient can select, and path information to navigate the question list. The survey questions probe into why a patient's weight, blood pressure, pulse rate and/or other measurements may be abnormal or unexpected, and provide the clinical user with additional information about the patient's condition. Reflexive surveys are initiated by rules applied to patient physiological measurements and patient responses to subjective questions.

In one embodiment, the reflexive survey is sent to the third party. This can be helpful as the third party, e.g. a family member, a care giver, etc., may be in a better position to notice changes in the patient, such as depression, which might be contributing to the identified abnormal condition of the patient.

With continuing reference to FIG. 1 and further reference to FIG. 2, the educational server automatically delivers educational content related to at least one of the surveys, vital sign measurements, health evaluation, or so forth. The educational content is arranged in a plurality of content sessions 150, 152, . . . cooperatively directed toward achieving a patient health management educational goal. The content sessions 150, 152, . . . are directed toward different health management educational goals. For example, different content sessions may be provided that are directed toward: reducing weight; stopping smoking; learning to follow a dietary restriction such as a low-salt diet; learning to follow a dietary requirement such as a high-fiber diet; performing a physical exercise; and so forth. The number of content sessions 150, 152, . . . can vary between one content session, to five, ten, or more content sessions. The content sessions can include various types of content, such as: pre-recorded audio/video content; textual content; interactive survey, quiz, questionnaire, or test content; pre-recorded step-by-step interactive audio/video content; and so forth.

The content may also be critical event content such as counsel actions to be taken in response to a monitored abnormality such as cardiac aristhma, sudden blood pressure drop, cardiac arrest, stroke, etc. This content may be directed to the patient or a spouse or other personas at the same location. The content may counsel for long term life style changes, short term actions, e.g. until an ambulance arrives, reminders for reacting to intermittently occurring attacks, and the like.

The patient profile 140 may optionally include personalizing information 160 that may include name, address, diagnosis, and so forth. In some embodiments, the personalizing information 160 is used to personalize content sessions. For example, a text-based content session may include name tag placeholders that are replaced by the personal name stored in the personalizing information 160 of the patient profile 140.

The educational content flow is controlled or regulated by at least one of the feedback paths 120, 122 from the patient or user. For example, if the user provides a set of responses to a survey via the user interface 30, the pre-processor 38 may grade the responses and generate a score indicating how well the patient scored on the survey. The score is then used to control content flow, for example by showing a remedial video of the patient scored low indicating lack of comprehension. As another example, if the input includes biometric parameter measurements acquired by the biometric devices 82 over a period of time, the first pre-processor 130 may perform unit conversion, time-averaging, peak-detection, or other pre-processing of the biometric measurements. Optionally, the inputs provided by a patient via the user interface 30 or by the biometric devices 82 operatively connected with the patient are stored in a patent records portion 162 of the patient profile 130.

Educational content is delivered to the user by a rules based content flow engine 170 based on at least the first feedback input 120 received by the measurement server 76 and optionally pre-processed by the first pre-processor 130, and the second feedback input 122 received by the survey server 78 and optionally pre-processed by the second pre-processor 132; and further based on content flow rules.

Maintenance of the educational server 80 is suitably performed by an administrator, for example, via the host center terminal 98. The administrator may, for example, add content sessions, delete obsolete content sessions, modify or update content sessions, modify or update content flow rules, configure the patient profile format, and so forth. The patient profile 140 is suitably maintained in accordance with a diagnosis or other information provided by the patient's doctor or other medical personnel. In some embodiments, medical personnel such as doctors or nurses can generate and/or update the patient profile 140 by directly accessing the second server 42 via the first station terminal 20. In other embodiments, one or more system administrators perform all creation and updating of the patient profile 140 via the host station terminal 98, and in accordance with instructions from the patient's physician or other medical personnel.

As described above, the user interface 48 can employ substantially any hardware capable of providing content presentation in unmodified and/or augmented form and capable of providing feedback to the second server 42. For example, the user interface 48 can be embodied by hardware such as: a desktop computer; a laptop computer; a personal data assistant (PDA); a cellular telephone (i.e., cellphone); a television set having Internet connectivity integrally included and operated by a television remote control or other input device; a digital or analog television set having Internet connectivity provided by an add-on set-top unit and operated by a television remote control, set-top unit remote control, or other input device; or so forth. The components of the second server 42 can be embodied in various ways, such as by a centralized computer or computer server, a desktop computer, or so forth. In some embodiments, existing educational content presentation hardware, such as an analog or digital television set, is modified or augmented by a set-top box that enables the television set to be used as a user interface for accessing the Internet or another digital network.

In the manner described above, the medically related educational materials are sent to the patients automatically. The automatic transmission of educational materials can be responsive to any information to which the system has access such as the monitored physiological conditions, survey answers, and the like. Moreover, the system described above is responsive to a lack of change or to progress in addressing a physiological condition, such as an overweight patient, steadily reducing his weight. The system can also respond to mile posts along a self improvement program, such as reducing blood pressure 5 points, losing 10 pounds, or the like. The educational service automatically sends out encouraging or reinforcing information to encourage the patient to continue his current course of self improvement. As a result, fewer trips to the hospitals and fewer hospitalizations are required because triggering events are detected earlier in the chain of events and patients are educated accordingly to adjust damaging behavior.

With continuing reference to FIG. 2 and further reference to FIG. 3, in a relatively centralized example arrangement of components of the health management system 10, the second server 42 which includes at least corresponding video server 74, measurement server 76, and educational server 78, is a centralized server that services in the manner described above a plurality of patients at second station locations $14_1$, $14_2$, $14_3$, . . . , $14_n$. Each patient has a corresponding personalized patient profile $140_1$, $140_2$, $140_3$, . . . , $140_n$. Communication between the patients and the remote centralized second server 42 is achieved by a wired or wireless network connection 56. For example, the network connection 56 can be a secure high-speed wireless or wired Internet link. The network connection 56 is advantageously a secure link because private medical information may be conveyed across the network connection 56. However, unsecured connections can also be used. In some embodiments, a patient may have more than one user interface. For example, if the second server 42 is accessible by a high-speed Internet connection, then the user may be able to access the second server 42 via the patient's home computer, personal data assistant (PDA), Internet-enabled cellular telephone, television set having Internet connectivity integrally included and operated by a television remote control, television set having Internet connectivity provided by an add-on set-top unit and operated by a television remote control, or other Internet-capable device. If the second server 42 is accessible by a cable television network, cellular telephone network, or so forth, then the user may be able to access the second server 42 by a respective cable television set, cellular telephone (i.e., cellphone), or so forth.

With continuing reference to FIG. 2 and further reference to FIG. 4, in a relatively decentralized example arrangement of components of the health management system 10, the second server 42, which includes at least corresponding video server 74, measurement server 76, and educational server 78, and the user interface 48 are embodied by a patient computer 190, personal data assistant (PDA), or other digital electronic device disposed at the dwelling of the patient or carried with the patient or otherwise readily accessed by the patient. The personalized educational content can be downloaded from the first station terminal 20 via a cable or satellite television network, cellular telephone network, the Internet, or otherwise loaded onto the patient computer 190, smart television, PDA, cellphone, or other device. Optionally, the host center terminal 98 may also include, for example, a secure Internet connection between a hospital computer and the patient computer 190 by which patient responses or biometric data are communicated to the doctor or hospital on a daily, weekly, or other time basis. Because in the embodiment of FIG. 3 an entire personalized instance of the health management system 10 is provided to the patient, there is typically only a single patient profile 140 corresponding to the single patient at that dwelling. It will be appreciated, however, that in the decentralized arrangement of FIG. 4, each patient will have his or her own personalized instance of the health management system 10 which will include that patient's personalized personal profile.

The centralized and decentralized arrangements or layouts of components of the health management system 10 depicted in FIGS. 3 and 4 are illustrative examples. Other arrangements can be used. For example, in some embodiments certain portions of the second server 42 may reside at a centralized server computer while certain other portions of the second server 42 may reside at the patient's computer. For example, the server may be located on a centralized server computer at the hospital or other centralized location and store the content sessions and patient profiles for a number of patients, but the rules-based content flow engine 170 may be an executable program downloaded to and executing on the patient's computer located at the patient's dwelling. In some embodiments, duplicate copies of portions of the second server 42 or portions thereof may reside at both a centralized server computer and the patient's computer. As an example of this latter arrangement, the patient's biometric measurements may be stored at the patient's computer for ready access by the patient, and also transmitted to a centralized server computer for review by the doctor.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A health management system comprising:
one or more memories at a central location which store a patient profile corresponding to each of a plurality of patients and a plurality of educational content sessions, the educational content sessions being directed toward helping patients achieve a health management goal;
at least one feedback path from each of the patients which provides at least one input; wherein the at least one feedback path includes a biometric device, the at least one input including biometric data, which includes a triggering event, acquired by the biometric device and wirelessly communicated to one or more processors from the biometric device; the one or more processors being at a patient site for each patient and programmed to:
monitor for critical events based on user input and/or biometric data received from the patients;
automatically select a plurality of the content sessions and a flow of the selected educational content sessions for each patient based on the patient profile, the input from the corresponding patient, and on content flow rules, the selected educational content sessions for at least one of the patients including critical event content selected in response to detecting a critical event, and the selected for at least one of the patients including a previously selected educational content session in response to the input from the corresponding patient; and,
communicate the selected educational content sessions into a user interface associated with the corresponding patient;
a display device at each user interface on which the selected educational content sessions are presented to the correspondent patient.

2. The health management system as set forth in claim 1, further including:
a survey server which generates a reflexive survey based on an item of interest of the triggering event and in response to the triggering event, which survey is sent to a corresponding patient.

3. The health management system as set forth in claim 2, wherein the survey includes:
a survey, quiz, test, or questionnaire including at least one question presented on the display device, the at least one input including a patient response via an input device.

4. The health management system as set forth in claim 2, wherein the triggering event includes:
a vital sign value measured by the biometric sensor beyond a predetermined threshold;
a vital sign value measured by the biometric sensor which matches a preselected criteria; and
a vital sign value measured by the biometric sensor beyond a dynamic threshold based on a prior measurement of the vital sign.

5. The health management system as set forth in claim 1, wherein the content rules include a rule calling for:
displaying a remedial session in response to a score on a test or survey indicative of a lack of comprehension;
displaying a behavior reinforcing message in response to reaching a milepost along a self-improvement program; and
displaying a motivational session responsive to a lack of progress along the self-improvement program.

6. A health management system including:
an educational server communicating with a plurality of patients, the educational server storing at least:
a plurality of content sessions directed toward achieving a health management goal, and
a plurality of patient profiles, each corresponding to a respective patient;

the educational server further including a content flow engine configured to control presentation of content sessions to each patient based on at least one feedback input from the patient and on content flow rules;
a plurality of biometric devices, the at least one feedback input from the patient being provided by at least one of the plurality of biometric devices which is monitoring the patient;
a survey server which generates a reflexive survey in response to a triggering event included in biometric data received from the plurality of biometric devices, the survey based on an item of interest of the triggering event; and
a measurement server which monitors for the triggering event from at least one of the biometric devices and a manual patient input, the measurement server causing the content flow engine to select the content session in accordance with the triggering event and the patient profile of the corresponding patient.

7. The health management system as set forth in claim 6, wherein the triggering event includes:
a vital sign measurement value beyond a predetermined threshold;
a vital sign measurement value which matches a preselected criteria; and
a vital sign measurement value beyond a dynamic threshold based on a prior measurement of the vital sign.

8. The health management system as set forth in claim 6, wherein the biometric devices provides the feedback input to the measurement server.

9. The health management system as set forth in claim 6, wherein the biometric devices provide the feedback input to the measurement server automatically.

10. The health management system as set forth in claim 6, wherein at least one of the biometric devices monitor the patient continuously.

11. The health management system as set forth in claim 6, further including:
a plurality of patient stations each connected with the educational server to generate and provide the feedback input electronically from at least one of the biometric devices to trigger the content flow engine to select the content session for the corresponding patient.

12. The health management system as set forth in claim 11, wherein the survey server generates unique surveys for each patient based on the manual patient input, the feedback from the biometric devices and the patient profile.

13. The health management system as set forth in claim 6, wherein the educational server presents a plurality of the content sessions to at least one of the patients, a flow of the sessions being controlled based on the biometric device feedback input.

14. The health management system as set forth in claim 6, wherein the educational server sends the content sessions to a television of each patient automatically for display.

15. A health management method comprising:
presenting a series of educational content sessions on a video device to motivate a patient in a self-improvement program;
receiving physiological condition inputs of interest over a period of time of the patient automatically from a biometric monitoring device;
analyzing the physiological condition inputs received from the biometric monitoring device received over the period of time;

automatically controlling a flow of one or more educational content sessions based on the analyzed physiological condition inputs and on content flow rules, including:
displaying a remedial session in response to a score on a test or survey indicative of a lack of comprehension;
displaying a behavior reinforcing message in response to reaching a milepost along a self-improvement program;
displaying a motivational session responsive to a lack of progress along the self-improvement program;
generating a reflexive survey in response to a triggering event in the physiological condition input; and
presenting the survey on the video device of the patient.

16. The health management method as set forth in claim 15, wherein the triggering event includes one of:
a vital sign measurement value beyond a predetermined threshold;
a vital sign measurement value which matches a preselected criteria; and
a vital sign measurement value a beyond a dynamic threshold based on a prior measurement of the vital sign.

17. A health management system comprising:
a plurality of patient stations, each patient station including:
an audio/visual display device which displays educational content sessions and surveys,
an input device by which a patient inputs answers to surveys,
a physiological monitoring device which measures at least one physiological parameter of the patient,
a control module which:
receives the educational content sessions and surveys,
supplies the content sessions and surveys to the display device,
receives the answers from the input device, and
receives the at least one physiological parameter from the physiological monitoring device;
a host center remote from the patient stations, the host center including:
a measurement server which receives measured physiological parameters from the patient stations,
a survey server connected with the measurement server, the survey server generating the surveys in response to received physiological parameters and survey answers,
a patient profile memory which stores a medical profile for each patient,
an educational server which selects and controls a flow of the content sessions to each patient station in accordance with the medical profile of the corresponding patient, the physiological parameters received from the patient station of the corresponding patient, and the survey answers received from the corresponding patient; and
a plurality of care provider stations remote from and connected with the host center, each care provider station including:
a work station which inputs information and receives information from the host center.

* * * * *